United States Patent [19]

Keil et al.

[11] Patent Number: 4,820,331
[45] Date of Patent: Apr. 11, 1989

[54] CYCLOHEXENONE DERIVATIVES USEFUL FOR REGULATING PLANT GROWTH

[75] Inventors: Michael Keil, Freinsheim; Ulrich Schirmer, Heidelberg; Dieter Kolassa, Ludwigshafen; Juergen Kast, Iggelheim; Wilhelm Rademacher; Johann Jung, both of Limburgerhof, all of Fed. Rep. of Germany

[73] Assignee: BASF Aktiengesellschaft, Ludwigshafen, Fed. Rep. of Germany

[21] Appl. No.: 128,451

[22] Filed: Dec. 3, 1987

[51] Int. Cl.$^4$ .................. A01N 43/16; A01N 35/02; C07D 309/12; C07C 49/543
[52] U.S. Cl. ........................... 71/88; 71/106; 71/107; 71/123; 549/416; 560/255; 560/231; 560/228; 560/107; 560/106; 568/377; 568/376; 568/329
[58] Field of Search .............. 568/377, 376, 329; 549/416; 560/106, 107, 228, 231, 255; 71/88, 106, 107, 123

[56] References Cited

U.S. PATENT DOCUMENTS

| | | | |
|---|---|---|---|
| 4,560,403 | 12/1985 | Motojima et al. | 71/106 |
| 4,584,013 | 4/1986 | Brunner | 71/94 |
| 4,744,820 | 5/1988 | Keil et al. | 568/377 |

Primary Examiner—Nicky Chan
Attorney, Agent, or Firm—Keil & Weinkauf

[57] ABSTRACT

Cyclohexenone derivatives of the general formula

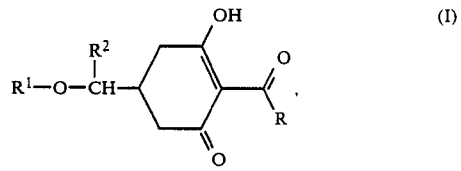

where R is $C_1$–$C_6$-alkyl, cyclopropyl, phenyl or $C_2$–$C_6$-alkoxyalkyl, $R^1$ is hydrogen, tetrahydropyran-2-yl, benzoyl or unsubstituted or halo-substituted $C_1$–$C_6$-alkanoyl, and $R^2$ is hydrogen or $C_1$–$C_6$-alkyl, and phytophysiologically tolerable salts thereof, and their use for regulating plant growth.

13 Claims, No Drawings

CYCLOHEXENONE DERIVATIVES USEFUL FOR REGULATING PLANT GROWTH

The present invention relates to novel cyclohexenone derivatives I, their use as agents for regulating the growth of plants, and a process for regulating plant growth.

EP-A-123 001 and EP-A-126 713 disclose that certain 2-acyl-3-hydroxycyclohex-2-en-1-ones influence plant growth.

We have now found that cyclohexenone derivatives of the formula I

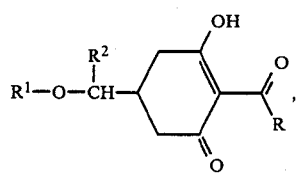

where R is $C_1$–$C_6$-alkyl, cyclopropyl, phenyl or $C_2$–$C_6$-alkoxyalkyl, $R^1$ is hydrogen, tetrahydropyran-2-yl, benzoyl or unsubstituted or halosubstituted $C_1$–$C_6$-alkanoyl, and $R^2$ is hydrogen or $C_1$–$C_6$-alkyl, and phytophysiologically tolerable salts thereof, have advantageous properties as growth regulators and are tolerated by plants. Use of the compounds as growth regulators is subject to the principles disclosed for compounds having a similar action, e.g., in the abovementioned publications.

Specifically, the substituents in formula I have the following meanings:

R=branched or straight-chain $C_1$–$C_6$-alkyl, preferably $C_1$–$C_5$-alkyl, such as methyl, ethyl, n-propyl, n-butyl and n-pentyl;

cyclopropyl;

phenyl;

$C_2$–$C_6$alkoxyalkyl, preferably $C_2$–$C_4$-alkoxyalkyl, such as methoxymethyl, ethoxymethyl, n-propoxymethyl, isopropoxymethyl, 1-methoxyethyl, 2-methoxyethyl, 1-ethoxyethyl, 2-ethoxyethyl, 1-methoxy-n-propyl, 2-methoxy-n-propyl, 3-methoxy-n-propyl, 1-methoxyisopropyl and 2-methoxyisopropyl, 2-methoxyethyl being particularly preferred;

$R^1$=hydrogen;

branched or straight-chain $C_1$–$C_6$-alkanoyl, preferably straight-chain $C_1$–$C_5$-alkanoyl, such as formyl, acetyl, n-propionyl, n-butyryl, valeryl and caproyl;

halogen-substituted, branched or straight-chain $C_1$–$C_6$-alkanoyl, preferably $C_2$- and $C_3$-alkanoyl mono- to trisubstituted by chlorine, such as chloroacetyl, dichloroacetyl, trichloroacetyl, 2-chloropropionyl and 3-chloropropionyl;

benzoyl;

tetrahydropyran-2-yl;

$R^2$=hydrogen;

branched or straight-chain $C_1$–$C_6$-alkyl, preferably branched or straight-chain $C_1$–$C_3$-alkyl, such as methyl, ethyl, n-propyl and isopropyl.

Suitable salts of compounds of the formula I are phytophysiologically tolerable salts, for example of alkali metals, especially potassium or sodium, alkaline earth metals, especially calcium, magnesium or barium, further, of manganese, copper, zinc or iron, and ammonium, phosphonium, sulfonium or sulfoxonium salts, e.g., ammonium, tetraalkylammonium, benzyltrialkylammonium, trialkylsulfonium and trialkylsulfoxonium salts.

The cyclohexenone derivatives of the formula I may be prepared by reacting a compound of the formula II

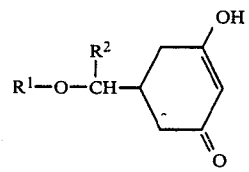

in conventional manner with an acid chloride R—COCl in the presence of a base, for example triethylamine, pyridine, sodium hydroxide or potassium carbonate, to give the enol ester, followed by rearrangement in the presence of an acidic or basic catalyst in an inert solvent (e.g., ethyl acetate, toluene) at from 0° to 100° C. Examples of acidic catalysts are aluminum chloride and iron chloride; examples of basic catalysts are preferably imidazole derivatives, e.g., imidazole, or pyridine derivatives, such as 4-N,N-dimethylaminopyridine.

The alcohols, i.e., those compounds in which $R^1$ is hydrogen, are advantageously obtained from the corresponding compounds initially containing a protective group. This protective group may for instance be tert-butyl, tetrahydropyran-2-yl or benzoyl, which is split off in conventional manner with aid of an acid, e.g., hydrochloric acid, sulfuric acid or phosphoric acid, or (in the case of benzoyl) hydrogenolytically, e.g., with hydrogen in the presence of Pd/C. Reduction of suitable precursors with $NaBH_4$ also gives the alcohols according to the invention:

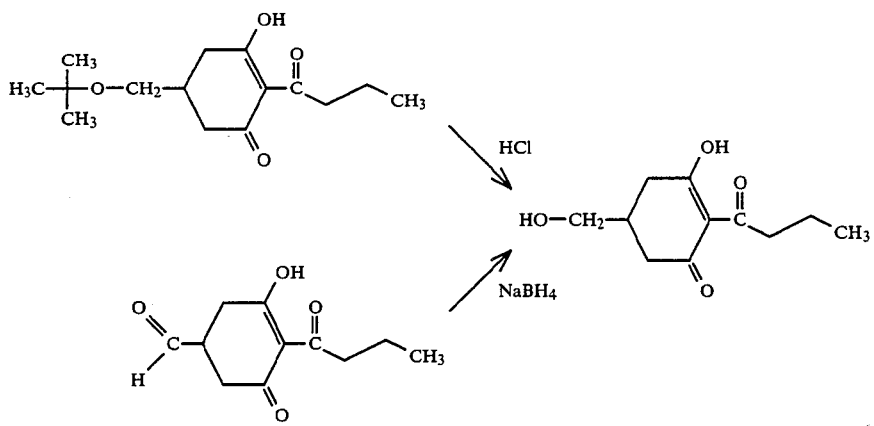

The precursors required for the reaction may be prepared in accordance with following scheme:

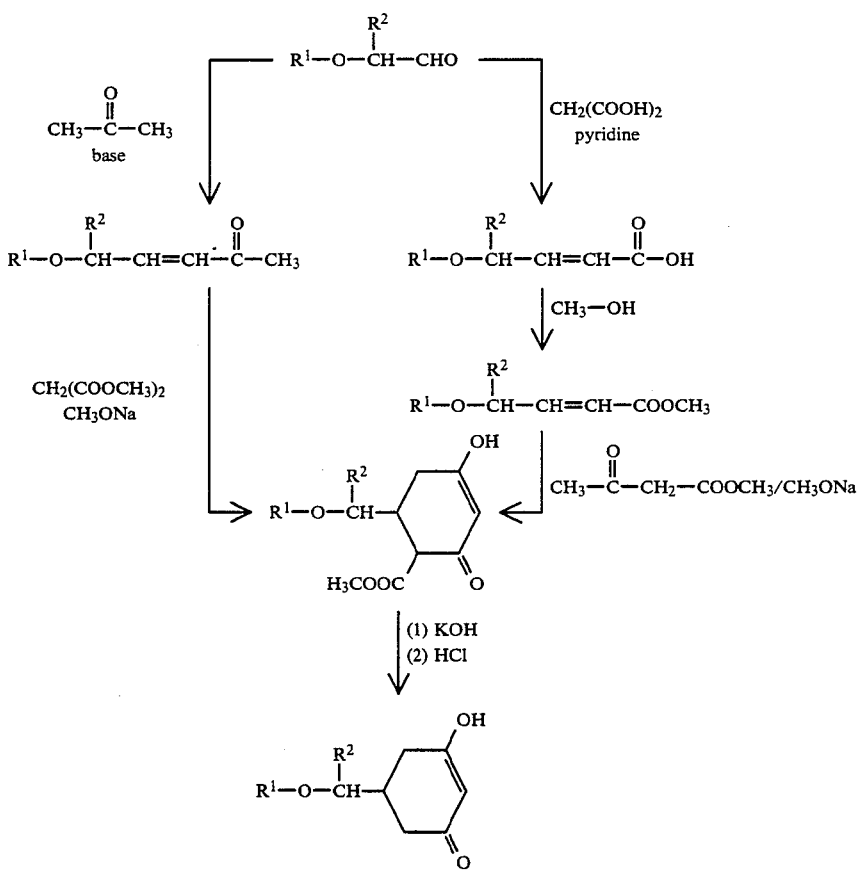

MANUFACTURING EXAMPLES

Example 1

0.1 g of sodium borohydride was added to 2.0 g of 2-butyryl-5-formyl-3-hydroxycyclohex-2-en-1-one in 30 ml of aqueous tetrahydrofuran; the mixture was stirred for 2 hours at 25° C. The mixture was then diluted with water, extracted several times with diethyl ether, dried and concentrated. There was obtained 1.5 g of 2-butyryl-3-hydroxy-5-hydroxymethylcyclohex-2-en-1-one (compound no. 3).

Example 2

At 0° to 10° C., 600 ml of concentrated hydrochloric acid was added to a solution of 44.6 g of 2-butyryl-5-tert-butoxymethyl-3-hydroxycyclohex-2-en-1-one in ethanol. After 2 hours the mixture was concentrated, and the residue was taken up in dichloromethane and extracted by shaking with water. After concentration there was obtained 26.2 g of 2-butyryl-3-hydroxy-5-hydroxymethylcyclohex-2-en-1-one as a pale yellow oil (compound no. 3).

The $^1$H-NMR spectra suitable for characterizing and confirming the structure of the compounds according to the invention were taken in deuterochloroform as solvent, with tetramethylsilane as internal standard. The $^1$H chemical shifts are given in ppm; only the characteristic signals are mentioned. The following abbreviations apply for the signal structure:

s=singlet, d=doublet, t=triplet, q=quartet, m=multiplet.

TABLE

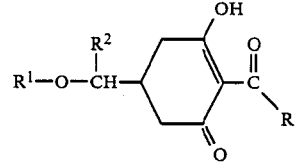

(I)

| Compound No. | R | R² | R¹ | δ [ppm] |
|---|---|---|---|---|
| 1 | CH₃ | H | H | 1.9–2.9 (m); 2.61 (s); 3.67 (m) |
| 2 | C₂H₅ | H | H | 1.12 (t); 3.04 (q); 3.62 (t) |
| 3 | n-C₃H₇ | H | H | 0.98 (t); 3.01 (t); 3.64 (m) |
| 4 | n-C₄H₉ | H | H | |
| 5 | n-C₅H₁₁ | H | H | |
| 6 | cyclopropyl | H | H | 1.12 (m); 1.28 (m); 3.58 (m) |
| 7 | phenyl | H | H | |
| 8 | 2-methoxyethyl | H | H | |
| 9 | CH₃ | CH₃ | H | |
| 10 | C₂H₅ | CH₃ | H | |
| 11 | n-C₃H₇ | CH₃ | H | 0.98 (t); 1.25 (d); 3.76 (m) |
| 12 | n-C₄H₉ | CH₃ | H | |
| 13 | cyclopropyl | CH₃ | H | |
| 14 | phenyl | CH₃ | H | |
| 15 | 2-methoxyethyl | CH₃ | H | |
| 16 | C₂H₅ | C₂H₅ | H | |
| 17 | n-C₃H₇ | C₂H₅ | H | 1.04 (m); 2.99 (t); 3.44 (m) |
| 18 | C₂H₅ | i-C₃H₇ | H | |
| 19 | n-C₃H₇ | i-C₃H₇ | H | |
| 20 | C₂H₅ | H | CH₃CO | 1.13 (t); 2.11 (s); 3.04 (q) |
| 21 | n-C₃H₇ | H | CH₃CO | 0.98 (t); 2.08 (s); 4.04 (m) |
| 22 | C₂H₅ | H | C₂H₅CO | 1.14 (m); 3.07 (q); 4.16 (q) |
| 23 | n-C₃H₇ | H | C₂H₅CO | 0.99 (t); 1.15 (t); 3.02 (t) |
| 24 | C₂H₅ | H | n-C₃H₇CO | |
| 25 | n-C₃H₇ | H | n-C₃H₇CO | 0.98 (m); 3.02 (t); 4.05 (m) |
| 26 | C₂H₅ | H | n-C₅H₁₁CO | |
| 27 | n-C₃H₇ | H | n-C₅H₁₁CO | 0.91 (t); 0.98 (t); 4.07 (d) |
| 28 | C₂H₅ | H | HCO | |
| 29 | n-C₃H₇ | H | HCO | |
| 30 | n-C₄H₉ | H | HCO | |
| 31 | C₂H₅ | H | Cl—CH₂CO | |
| 32 | n-C₃H₇ | H | Cl—CH₂CO | 0.98 (t); 4.10 (s); 4.18 (m) |
| 33 | C₂H₅ | H | Cl—CH₂CH₂CO | 1.13 (t); 3.08 (q); 3.76 (t) |
| 34 | n-C₃H₇ | H | Cl—CH₂CH₂CO | 0.98 (t); 3.01 (t); 3.77 (t) |
| 35 | C₂H₅ | H | Cl₃CCO | |
| 36 | n-C₃H₇ | H | Cl₃CCO | 0.98 (t); 3.03 (t); 4.32 (m) |
| 37 | C₂H₅ | H | C₆H₅CO | |
| 38 | n-C₃H₇ | H | C₆H₅CO | |
| 39 | C₂H₅ | H | tetrahydropyran-2-yl | |
| 40 | n-C₃H₇ | H | tetrahydropyran-2-yl | |
| 41 | CH₃ | CH₃ | CH₃CO | |
| 42 | C₂H₅ | CH₃ | CH₃CO | |
| 43 | n-C₃H₇ | CH₃ | CH₃CO | 0.98 (t); 1.38 (d); 2.09 (s) |
| 44 | n-C₄H₉ | CH₃ | CH₃CO | |
| 45 | n-C₅H₁₁ | CH₃ | CH₃CO | |
| 46 | cyclopropyl | CH₃ | CH₃CO | |
| 47 | phenyl | CH₃ | CH₃CO | |
| 48 | 2-methoxyethyl | CH₃ | CH₃CO | |
| 49 | C₂H₅ | i-C₃H₇ | CH₃CO | |
| 50 | n-C₃H₇ | i-C₃H₇ | CH₃CO | |
| 51 | CH₃ | H | CH₃CO | 2.09 (s); 2.61 (s); 4.03 (m) |
| 52 | n-C₄H₉ | H | CH₃CO | |
| 53 | CH₃ sodium salt | H | H | |
| 54 | C₂H₅ sodium salt | H | H | |
| 55 | C₂H₅ potassium salt | H | H | |
| 56 | C₂H₅ tetrabutylammonium salt | H | H | |
| 57 | n-C₃H₇ sodium salt | H | H | |

TABLE-continued

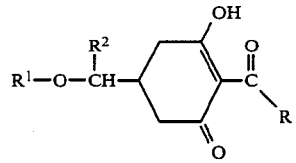

| Compound No. | R | R² | R¹ | δ [ppm] |
|---|---|---|---|---|
| 58 | n-C₃H₇ potassium salt | H | H | |
| 59 | n-C₃H₇ tetrabutylammonium salt | H | H | |
| 60 | cyclopropyl sodium salt | H | H | |
| 61 | n-C₃H₇ sodium salt | C₂H₅ | H | 0.83 (t); 0.86 (t); 3.08 (m) |
| 62 | n-C₃H₇ | C₂H₅ | CH₃CO | 2.19 (s). 2.99 (t); 4.83 (m) |
| 63 | n-C₃H₇ potassium salt | CH₃ | H | 0.80 (t). 0.98 (d); 3.35 (m) |
| 64 | n-C₃H₇ sodium salt | CH₃ | H | 0.82 (t); 1.02 (d); 3.36 (m) |
| 65 | cyclopropyl | H | CH₃CO | 1.14 (m); 1.31 (m); 2.09 (s) |

The cyclohexenone derivatives of the formula I may have a variety of influences on practically all plant development stages, and may therefore be used as growth regulators. The diversity of action of growth regulators depends especially on (a) the type and variety of plant;

(b) the time applied, with reference to the development stage of the plants and the time of the year;

(c) the place and method of application (seed treatment, soil treatment, or application to foliage);

(d) climatic factors, e.g., temperature, amount of precipitate, day length and light intensity;

(e) soil conditions (including fertilization);

(f) the formulation of the active ingredient; and (g) the concentration at which the active ingredient is applied.

A description of some of the various possibilities of using the growth regulators according to the invention in agriculture and horticulture is given below.

A. Vegetative plant growth can be inhibited to a considerable extent, a fact which is manifested particularly in a reduction in plant height. The treated plants thus have a compact habit; furthermore, the leaf color is darker.

Of advantage in practice is for example the reduction in grass growth on roadsides, canal embankments and on areas such as parks, sportsgrounds, fruit orchards, lawns and airfields, thus reducing expensive and time-consuming mowing.

A further feature of economic interest is the increase in the rigor of crops which tend to lodge, such as cereals, Indian corn, sunflowers and soybeans. The shortening and strengthening of the stem thus caused reduces or eliminates the danger of lodging under unfavorable weather conditions.

The use of growth regulators is also important for inhibiting plant height and changing the time of ripening in cotton. It is thus possible for this important crop to be harvested completely mechanically.

Growth regulators may also increase or inhibit lateral branching. This is of interest when, for instance in tobacco plants, it is desired to inhibit the formation of lateral shoots (suckers) in favor of leaf development.

With growth regulators, it is possible for instance in winter rape to considerably increase the resistance to freeze injury. On the one hand, upward growth and the development of a too luxuriant (and thus particularly frost-susceptible) leaf or plant mass are inhibited; on the other, the young rape plants are kept, in spite of favorable growth conditions, in the vegetative development stage before winter frosts begin. The danger of freeze injury is thus eliminated in plants which tend to lose prematurely their inhibition to bloom and pass into the generative phase. In other crops, too, e.g., winter cereals, it is advantageous if the plants are well tillered in the fall as a result of treatment with the compounds according to the invention, but enter winter with not too lush a growth. This is a preventive measure against increased susceptibility to freeze injury and—because of the relatively low leaf or plant mass—attack by various (especially fungus) diseases. The inhibition of vegetative growth also makes closer planting possible in numerous crops, which means an increase in yield, based on the area cropped.

B. Better yields both of plant parts and plant materials may be obtained with the active ingredients according to the invention. It is thus for instance possible to induce increased formation of buds, blossom, leaves, fruit, seed grains, roots and tubers, to increase the sugar content of sugarbeets, sugarcane and citrus fruit, to raise the protein content of cereals and soybeans, and to stimulate the increased formation of latex in rubber trees.

The cyclohexenone derivatives of the formula I may raise the yield by influencing plant metabolism or by promoting or inhibiting vegetative and/or generative plant growth.

C. It is also possible with growth regulators to shorten or lengthen growth stages and to accelerate or retard the ripening process in plant parts either before or after harvesting.

A factor of economic interest is for example the facilitation of harvesting made possible by a chemical, temporally concentrated loosening (abscission) of the adherence of stalks to the branches of citrus fruit, olive trees, and other kinds of pomes, drupes and indehiscent fruit. The same mechanism, i.e., promotion of the formation of separation layers between fruit or leaf and stem of the plant, is also essential for a readily controllable defoliation of crop plants.

D. Further, transpiration in crop plants may be reduced with growth regulators. This is particularly important for plants growing in agricultural areas which are expensive to irrigate, e.g., in arid or semi-arid areas. Irrigation frequency can be reduced by using the compounds according to the invention, making for lower costs. As a result of the use of growth regulators, the water available can be better utilized, because, inter alia, the size of the stomata opening is reduced;
a thicker epidermis and cuticle are formed;
penetration of the soil by the roots is improved;
the micro-climate in the stand is favorably influenced by the more compact growth.

The active ingredients to be used in accordance with the invention may be applied not only to the seed (as a disinfectant), but also to the soil, i.e., via the roots, and to the foliage by spraying.

As a result of the good crop plant tolerance, the application rate may vary considerably.

When seed is treated, active ingredient amounts of from 0.001 to 50, and preferably from 0.01 to 10, g per kg of seed are generally needed.

When the soil or foliage is treated, rates of from 0.01 to 10, and preferably from 0.05 to 3, kg per hectare are generally considered to be sufficient.

The novel substances can be employed in the form of conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene, benzene), chlorinated aromatics (e.g., chlorobenzenes), paraffins (e.g., crude oil fractions), alcohols (e.g., methanol, butanol), amines (eg., ethanolamine) N,N-dimethylformamide, and water; solid carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates); and dispersants such as lignin, sulfite waste liquors and methylcellulose. It is preferred to apply the active ingredients according to the invention in aqueous solution, if desired with the addition of water-miscible organic solvents such as methanol or other lower alcohols, acetone, N,N-dimethylformamide on N-methylpyrrolidone. The fungicides generally contain from 0.1 to 95, and preferably from 0.5 to 90, wt% of active ingredient.

The formulations, or the ready-to-use preparations prepared therefrom, such as solutions, emulsions, suspensions, powders, dusts, pastes or granules, are applied in known manner, for example preemergence, postemergence, or as seed disinfectants.

Examples of formulations are given below.

I. 20 parts by weight of the compound of Example 3 is well mixed with 3 parts by weight of the sodium salt of diisobutylnaphthalene-αsulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

II. 3 parts by weight of the compound of Example 3 is intimately mixed with 97 parts by weight of particulate kaolin. A dust is obtained containing 3% by weight of the active ingredient.

III. 30 parts by weight of the compound of Example 3 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

IV. 40 parts by weight of the compound of Example 3 is intimately mixed with 10 parts of the sodium salt of a phenolsulfonic acid-urea-formaldehyde condensate, 2 parts of silica gel and 48 parts of water to give a stable aqueous dispersion. Dilution in 100,000 parts by weight of water gives an aqueous dispersion containing 0.04 wt% of active ingredient.

V. 20 parts of the compound of Example 3 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

VI. 90 parts by weight of the compound of Example 3 is mixed with 10 parts by weight of N-methyl-α-pyrrolidone. A mixture is obtained which is suitable for application in the form of very fine drops.

VII. 20 parts by weight of the compound of Example 3 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

VIII. 20 parts by weight of the compound of Example 3 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IX. 20 parts by weight of the compound of Example 3 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

In these application forms, the agents according to the invention may also be present together with other active ingredients, for example herbicides, insecticides, other growth regulators, and fungicides, and may furthermore be mixed and applied together with fertilizers. Admixture with other growth regulator mixtures gives synergistic effects, i.e., the action of the combination product is greater than the added actions of its components.

Examples of fungicides which may be combined with the novel compounds are:
sulfur,
dithiocarbamates and their derivatives, such as
ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate,
ammonia complex of zinc N,N'-propylenebisdithiocarbamate,
zinc N,N'-propylenebisdithioccarbamate and N,N'-polypropylenebis(thiocarbamyl)disulfide;
nitro derivatives, such as
dinitro(1-methylheptyl)-phenyl crotonate,
2-sec-butyl-4,6-dinitrophenyl 3,3-dimethylacrylate,
2-sec-butyl-4,6-dinitrophenyl isopropylcarbonate and diisopropyl 5-nitroisophthalate;
heterocyclic substances, such as
2-heptadecylimidazol-2-yl acetate,
2,4-dichloro-6-(o-chloroanilino)-s-triazine,
O,O-diethyl phthalimidophosphonothioate,
5-amino-1-[-bis-(dimethylamino)-phosphinyl]-3-phenyl-1,2,4-triazole,
2,3-dicyano-1,4-dithioanthraquinone,
2-thio-1,3-dithio[4,5-b]quinoxaline,
methyl 1-(butylcarbamyl)-2-benzimidazolecarbamate,
2-methoxycarbonylaminobenzimidazole,
2-(fur-2-yl)-benzimidazole,
2-(thiazol-4-yl)benzimidazole,
N-(1,1,2,2-tetrachloroethylthio)-tetrahydrophthalimide,
N-trichloromethylthiotetrahydrophthalimide,
N-trichloromethylthiophthalimide,
N-dichlorofluoromethylthio-N',N'-dimethyl-N-phenyl-sulfuric acid diamide,
5-ethoxy-3-trichloromethyl-1,2,3-thiadiazole,
2-thiocyanatomethylthiobenzothiazole,
1,4-dichloro-2,5-dimethoxybenzene,
4-(2-chlorophenylhydrazono)-3-methyl-5-isoxazolone,
2-thiopyridine 1-oxide,
8hydroxyquinoline and its copper salt,
2,3-dihydro-5-carboxanilido-6-methyl-1,4-oxathiyne,
2,3-dihydro-5-carboxanilido-6-methyl-1,4-oxathiyne 4,4-dioxide,
2-methyl-5,6-dihydro-4H-pyran-3-carboxanilide,
2-methylfuran-3-carboxanilide,
2,5-dimethylfuran-3-carboxanilide,
2,4,5-trimethylfuran-3-carboxanilide,
2,5-dimethyl-N-cyclohexylfuran-3-carboxamide,
N-cyclohexyl-N-methoxy-2,5-diethylfuran-3-carboxamide,
2-methylbenzanilide,
2-iodobenzanilide,
N-formyl-N-morpholine-2,2,2-trichloroethylacetal,
piperazine-1,4-diylbis-(1-(2,2,2-trichloroethyl)-formamide),
1-(3,4-dichloroanilino)-1-formylamino-2,2,2-trichloroethane,
2,6-dimethyl-N-tridecylmorpholine and its salts,
2,6-dimethyl-N-cyclododecylmorpholine and its salts,
N-[3-(p-tert.-butylphenyl)-2-methylpropyl]-cis-2,6-dimethylmorpholine,
N-[3-(p-tert.-butylphenyl)-2-methylpropyl]-piperidine,
1-[2-(2,4-dichlorophenyl)-4-ethyl-1,3-dioxolan-2-ylethyl]-1H-1,2,4-triazole,
1-[2-(2,4-dichlorophenyl-4-n-propyl-1,3-dioxolan-2-ylethyl]-1H-1,2,4-triazole,
N-(n-propyl)-N-(2,4,6-trichlorophenoxyethyl)-N'-imidazolyl-urea,
1-(4-chlorophenoxy)-3,3-dimethyl-1-(1H-1,2,4-triazol-1-yl)-butan-2-one,
1-(4-chlorophenoxy)-3,3-dimethyl-1-(1H-1,2,4-triazol-1-yl)-butan-2-ol,
α-(2-chlorophenyl)-α-(4-chlorophenyl)-5-pyrimidinemethanol,
5-butyl-(2-dimethylamino-4-hydroxy-6-methylpyrimidine,
bis-(p-chlorophenyl)-3-pyridinemethanol,
1,2-bis-(3-ethoxycarbonyl-2-trioureido)-benzene,
1,2-bis-(3-methoxycarbonyl-2-thiouredio)-benzene,
and various fungicides, such as
dodecylguanidine acetate,
3-[3,5-dimethyl-2-oxycyclohexyl)-2-hydroxyethyl]-glutaramide,
hexachlorobenzene,
DL-methyl-N-(2,6-dimethylphenyl)-N-fur-2-yl alanate,
methyl DL-N-(2,6-dimethylphenyl)-N-(2'-methoxyacetyl)-alanate,
N-(2,6-dimethylphenyl)-N-chloroacetyl-DL-2-aminobutyrolactone,
methyl DL-N-(2,6-dimethylphenyl)-N-(phenylacetyl)-alanate,
5-methyl-5-vinyl-3-(3,5-dichlorophenyl)-2,4-dioxo-1,3-oxazolidine,
3-[3,5-dichlorophenyl]-5-methyl-5-methoxymethyl-1,3-oxazolidine-2,4-dione,
3-(3,5-dichlorophenyl)-1-isopropylcarbamylhydantoin,
N-(3,5-dichlorophenyl)-1,2-dimethylcyclopropane-1,2-dicarboximide,
2-cyano-[N-(ethylaminocarbonyl)-2-methoximino]-acetamide,
1-[2-(2,4-dichlorophenyl)-pentyl]-1H-1,2,4-triazole,
2,4-difluoro-α-(1H-1,2,4-triazol-1-ylmethyl)-benzhydryl alcohol.

Use Examples

To determine the growth-regulating properties of the candidate compounds, a culture medium was supplied with sufficient nutrients, and test plants were grown therein in plastic pots approx. 12.5 cm in diameter and having a volume of about 500 ml.

For the preemergence soil treatment, the candidate compounds were applied to the seedbed as aqueous formulations on the day of sowing; in the postemergency foliage treatment, the candidate compounds were applied to the plants as aqueous formulations.

The growth-regulating action observed was confirmed at the end of the experiment by measuring the growth height. The figures obtained were compared with those for untreated plants.

The commercial growth regulator chlormequat chloride (CCC) was used for comparison purposes. Not only was growth height reduced—the leaves also took on a more intense color. The increased chlorophyll content is indicative of a higher rate of photosynthesis, making for bigger yields.

TABLE

Spring barley, "Aramir" variety, preemergence (soil) treatment

| Compound No. | Conc. mg of comp./vessel | Growth height rel. |
| --- | --- | --- |
| | 1a | |
| untreated | — | 100 |
| CCC | 6 | 83.3 |
| 3 | 6 | 66.4 |
| | 1b | |
| untreated | — | 100 |
| CCC | 6 | 81.0 |
| 2 | 6 | 51.5 |
| 23 | 6 | 77.2 |
| 25 | 6 | 73.6 |

TABLE 2

Rice, "Bahia" variety, postemergence treatment

| Compound no. | Conc. mg of comp./vessel | Growth height rel. |
| --- | --- | --- |
| untreated | — | 100 |
| CCC | 1.5 | 101.8 |
| | 6 | 99.4 |
| 3 | 1.5 | 64.2 |
| | 6 | 48.5 |

TABLE 3

Spring barley, "Aramir" variety, postemergence (leaf) treatment

| Compound No. | Conc. mg of comp./vessel | Growth height rel. |
| --- | --- | --- |
| untreated | — | 100 |
| CCC | 6 | 84.6 |
| 2 | 6 | 71.5 |
| 3 | 6 | 64.9 |
| 23 | 6 | 70.1 |
| 25 | 6 | 74.4 |
| 27 | 6 | 69.8 |
| 32 | 6 | 71.2 |
| 34 | 6 | 70.1 |
| 36 | 6 | 71.5 |

TABLE 4

Lawnseed, "Tiergarten Mischung" variety, postemergence treatment

| Compound No. | Conc. mg of comp./vessel | Growth height rel. |
| --- | --- | --- |
| untreated | — | 100 |
| CCC | 1.5 | 99.6 |
| | 6 | 99.6 |
| 3 | 1.5 | 92.5 |
| | 6 | 85.3 |
| 27 | 1.5 | 93.2 |
| | 6 | 83.6 |

TABLE 5

Spring wheat, "Kolibri" variety, postemergence (leaf) treatment

| Compound No. | Conc. mg of comp./vessel | Growth height rel. |
| --- | --- | --- |
| untreated | — | 100 |
| CCC | 6 | 79.6 |
| 2 | 6 | 67.8 |
| 3 | 6 | 72.0 |
| 23 | 6 | 69.3 |
| 25 | 6 | 67.8 |
| 34 | 6 | 75.1 |
| 36 | 6 | 61.9 |

We claim:

1. A cyclohexenone derivative of the formula I

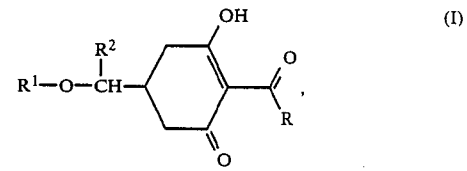

where R is $C_1$–$C_6$-alkyl, cyclopropyl, phenyl or $C_2$–$C_6$-alkyoxyalkyl, $R^1$ is hydrogen, tetrahydropyran-2-yl, benzoyl or unsubstituted or halosubstituted $C_1$–$C_6$-alkanoyl, and $R^2$ is hydrogen or $C_1$–$C_6$-alkyl, and phyto-physiologically tolerable salts thereof.

2. A cyclohexenone derivative of the general formula I as set forth in claim 1, where R is $C_1$–$C_5$-alkyl, cyclopropyl, phenyl or $C_2$–$C_4$-alkoxyalkyl, $R^1$ is hydrogen, tetrahydropyran-2-yl, benzoyl, straight-chain $C_1$–$C_5$-alkanoyl, or $C_2$–$C_3$-alkanoyl mono-, di- or tri-substituted by chlorine, and $R^2$ is hydrogen or $C_1$–$C_3$-alkyl, and phyto-physiologically tolerable salts thereof.

3. A cyclohexenone derivative of the formula I as defined in claim 1, wherein
R is ethyl or n-propyl,
$R^1$ is hydrogen, n-propyl, n-butyryl, chloroacetyl, trichloroacetyl or 3-chloropropionyl, and
$R^2$ is hydrogen.

4. The cyclohexenone derivative of the formula I as defined in claim 1 which is 5-hydroxymethyl-2-propionyl-cyclohexane-1,3-dione.

5. The cyclohexenone derivative of formula I as defined in claim 1 which is 5-hydroxymethyl-2-butyryl-cyclohexane-1,3-dione.

6. The cyclohexenone derivative of the formula I as defined in claim 1 which is 5-propionyloxymethyl-2-butyryl-cyclohexane-1,3-dione.

7. The cyclohexenone derivative of the formula I as defined in claim 1 which is 5-butyryloxymethyl-2-butyryl-cyclohexane-1,3-dione.

8. The cyclohexenone derivative of the formula I as defined in claim 1 which is 5-n-hexanoyloxymethyl-2-butyryl-cyclohexane-1,3-dione.

9. The cyclohexenone derivative of the formula I as defined in claim 1 which is 5-chloroacetyloxymethyl-2-butyryl-cyclohexane-1,3-dione.

10. The cyclohexenone derivative of the formula I as defined in claim 1 which is 5-(3-chloropropionyloxymethyl)-2-butyryl-cyclohexane-1,3-dione.

11. The cyclohexenone derivative of the formula I as defined in claim 1 which is 5-trichloroacetyloxymethyl-2-butyryl-cyclohexane-1,3-dione.

12. A composition for regulating the growth of plants which comprises: an effective amount of a cyclohexenone derivative of the formula I as set forth in claim 1 and inert additives.

13. A process for regulating the growth of plants which comprises: applying to the plants or their habitat an effective amount of the composition of claim 12.

* * * * *

UNITED STATES PATENT AND TRADEMARK OFFICE
CERTIFICATE OF CORRECTION

PATENT NO. : 4,820,331
DATED : April 11, 1989
INVENTOR(S) : KEIL et al

It is certified that error appears in the above-identified patent and that said Letters Patent is hereby corrected as shown below:

On the title page, add

--(30) Foreign Application Priority Data

Dec. 3, 1986  Fed. Rep. of Germany . . .  3641234--.

Signed and Sealed this

Twenty-third Day of January, 1990

Attest:

JEFFREY M. SAMUELS

*Attesting Officer*   *Acting Commissioner of Patents and Trademarks*